(12) United States Patent
Park et al.

(10) Patent No.: US 9,227,884 B2
(45) Date of Patent: Jan. 5, 2016

(54) METHOD OF PRODUCING SUBSTITUTE NATURAL GAS

(71) Applicant: HANWHA TECHWIN CO.,LTD., Changwon-Si (KR)

(72) Inventors: Hee-ho Park, Changwon (KR); Deok-jin Yun, Changwon (KR)

(73) Assignee: Hanwha Techwin Co., Ltd., Changwon-si (KR)

( * ) Notice: Subject to any disclaimer, the term of this patent is extended or adjusted under 35 U.S.C. 154(b) by 400 days.

(21) Appl. No.: 13/723,448

(22) Filed: Dec. 21, 2012

(65) Prior Publication Data

US 2013/0274354 A1    Oct. 17, 2013

(30) Foreign Application Priority Data

Apr. 13, 2012   (KR) .................... 10-2012-0038706

(51) Int. Cl.
    *C07C 27/00*    (2006.01)
    *C07C 1/04*     (2006.01)

(52) U.S. Cl.
    CPC ............... *C07C 1/0495* (2013.01); *C07C 1/041* (2013.01)

(58) Field of Classification Search
    CPC ............................ C07C 1/041; C07C 1/0495
    USPC ......................... 518/700, 702–704
    See application file for complete search history.

(56) References Cited

U.S. PATENT DOCUMENTS

| 7,232,472 B2 | 6/2007 | Kindig et al. |
| 8,128,728 B2 | 3/2012 | Tsangaris et al. |
| 2010/0028216 A1 * | 2/2010 | Park .............................. 422/105 |

FOREIGN PATENT DOCUMENTS

| JP | 2008-163257 A | 7/2008 |
| KR | 10-2004-0012730 A | 2/2004 |
| KR | 10-2004-0107746 A | 12/2004 |
| KR | 10-2008-0028409 A | 3/2008 |
| KR | 10-2009-0124784 A | 12/2009 |

OTHER PUBLICATIONS

Sun et al, Chinese abstract CN 1384044, Dec. 2002.*
Li et al, Chinese abstract CN 101074397, Nov. 2007.*

* cited by examiner

*Primary Examiner* — Jafar Parsa
(74) *Attorney, Agent, or Firm* — Sughrue Mion, PLLC

(57) ABSTRACT

Provided is a method of producing a substitute natural gas. The method includes: generating carbon monoxide and hydrogen using coal and a metal fuel; and generating methane from the generated carbon monoxide and hydrogen. Since the method supplies a metal fuel along with coal, generates hydrogen from the metal fuel, and supplies the hydrogen, the amount of coal needed to generate methane through methanation may be reduced and the amount of carbon dioxide ($CO_2$) generated when the coal is combusted may be reduced.

13 Claims, 2 Drawing Sheets

METHOD OF PRODUCING SUBSTITUTE NATURAL GAS

CROSS-REFERENCE TO RELATED PATENT APPLICATION

This application claims the priority from Korean Patent Application No. 10-2012-0038706, filed on Apr. 13, 2012, in the Korean Intellectual Property Office, the disclosure of which is incorporated herein by reference in its entirety.

BACKGROUND

1. Field

Apparatuses and methods consistent with exemplary embodiments relate to a method of producing a substitute natural gas (SNG) through methanation, and more particularly, to a method of producing an SNG by using a metal fuel.

2. Description of the Related Art

As demands for natural gases have recently increased, the use of a substitute natural gas (SNG) produced by gasifying coal, which is a fossil fuel, and generating methane through methanation is increasing.

However, while such an SNG is produced, a lot of carbon dioxide ($CO_2$) is also generated as a by-product. Since carbon dioxide is considered a greenhouse gas causing global warming, attempts to reduce carbon dioxide are required.

Also, since coal is a finite resource that could be exhausted someday, attempts to have a substitute for coal are also required.

SUMMARY

One or more exemplary embodiments may overcome the above disadvantages and other disadvantages not described above. However, it is understood that one or more exemplary embodiment are not required to overcome the disadvantages described above, and may not overcome any of the problems described above.

One or more exemplary embodiments provide a method of stably producing a substitute natural gas (SNG) while reducing the amount of coal used and reducing the amount of carbon dioxide ($CO_2$) generated when the coal is combusted.

According to an aspect of an exemplary embodiment, there is provided a method of producing an SNG, the method including: generating carbon monoxide and hydrogen using coal and a metal fuel; and generating methane from the generated carbon monoxide and hydrogen.

The generating of the carbon monoxide and the hydrogen may include: generating the carbon monoxide and primary hydrogen by gasifying the coal in a first gasification unit; generating secondary hydrogen by reacting the metal fuel in a second gasification unit; and supplying the secondary hydrogen generated in the second gasification unit to the first gasification unit.

The method may further include supplying heat generated from the generating of the secondary hydrogen in the second gasification unit to the first gasification unit.

The method may further include generating a metal oxide by reacting the metal fuel in the second gasification unit; and reducing and reusing the metal oxide as the metal fuel.

The metal fuel may include aluminum powder or magnesium powder.

The method may further include removing impurities from the generated carbon monoxide and hydrogen in a gas cleaning unit.

The generating of the carbon monoxide and the hydrogen may also include generating carbon monoxide and hydrogen by gasifying both the coal and the metal fuel in the first gasification unit.

The method may further include adding an alkaline material along with the metal fuel to the first gasification unit.

The metal fuel may include aluminum powder or magnesium powder, and the alkaline material may be selected from the group consisting of sodium hydroxide (NaOH), potassium hydroxide (KOH), and gallium.

The gasifying both the carbon monoxide and the hydrogen comprises may include generating the carbon monoxide and primary hydrogen by reacting the coal with water and oxygen and generating secondary hydrogen by reacting the metal fuel with water and a catalyst.

The method may further include generating heat from the generating the secondary hydrogen by reacting the metal fuel with the water and the catalyst.

The method may further include removing impurities from the generated carbon monoxide and hydrogen in a gas cleaning unit.

According to an aspect of an exemplary embodiment, there is provided a substitute natural gas producing device including: a first gasification unit which generates carbon monoxide and primary hydrogen using coal and a metal fuel; a second gasification unit which generates secondary hydrogen using a metal fuel, wherein the second gasification unit supplies the generated secondary hydrogen to the first gasification unit, a gas cleaning unit which removes impurities from the generated carbon monoxide and hydrogen; and a metanation unit which generates the substitute natural gas from the generated carbon monoxide and primary and secondary hydrogen.

The substitute natural gas producing device of claim 13, wherein the second gasification unit supplies heat generated from the generating of the secondary hydrogen in the second gasification unit to the first gasification unit.

The first gasification unit generates the carbon monoxide and primary hydrogen by reacting the coal with water and oxygen, and the second gasification generates secondary hydrogen by reacting the metal fuel with water and a catalyst.

According to an aspect of an exemplary embodiment, there is provided a substitute natural gas producing device including a gasification unit which generates carbon monoxide and hydrogen using coal and a metal fuel, a gas cleaning unit which removes impurities from the generated carbon monoxide and hydrogen, a metanation unit which generates the substitute natural gas from the generated carbon monoxide and primary and secondary hydrogen. The gasification unit is configured to intake alkaline material.

The metal fuel of the device may also include aluminum powder or magnesium powder, and the alkaline material is selected from the group consisting of sodium hydroxide, potassium hydroxide, and gallium.

BRIEF DESCRIPTION OF THE DRAWINGS

The above and other aspects will become more apparent by describing in detail exemplary embodiments thereof with reference to the attached drawings in which.

DETAILED DESCRIPTION

Figure 1:
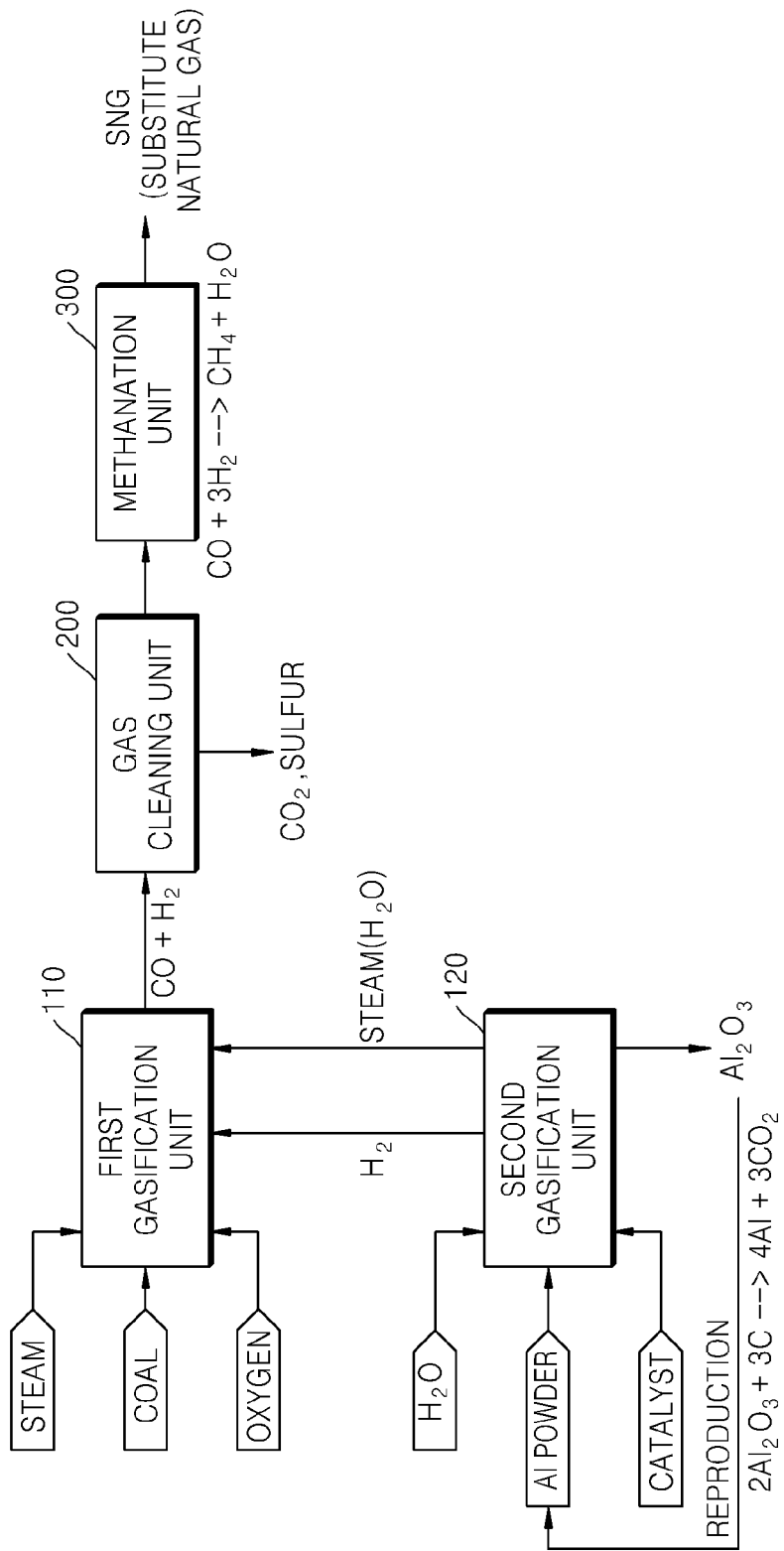
FIG. 1 is a block diagram illustrating a method of producing a substitute natural gas (SNG), according to an exemplary embodiment.

Hereinafter, exemplary embodiments will be described more fully with reference to the accompanying drawings so that a person having ordinary skill in the art to which the present inventive concept pertains can easily realize the exemplary embodiments. Like elements are denoted by like reference numerals throughout and a repeated explanation thereof will be omitted.

FIG. 1 is a block diagram for explaining a method of producing a substitute natural gas (SNG), according to an exemplary embodiment.

In FIG. 1, coal and a metal fuel are used as sources of carbon monoxide (CO) and hydrogen ($H_2$) from which methane ($CH_4$) is generated. That is, since not only the coal, which is a fossil fuel, but also the metal fuel is used as a raw material, source materials may be diversified, thereby preparing against the future exhaustion of fossil fuels.

The metal fuel may be aluminum (Al) or magnesium (Mg). The following explanation will be given assuming that aluminum powder is used. The metal fuel may generate hydrogen when reacting with water in an appropriate environment. When the metal fuel is aluminum, an exothermic reaction occurs according to the following process to generate hydrogen.

$$2Al + 3H_2O \rightarrow Al_2O_3 + 3H_2 \quad \text{(Equation 1)}$$

Accordingly, when hydrogen and heat generated in the reaction between the aluminum and the water are used, the amount of coal used may be reduced, energy needed to gasify the coal may be reduced, and the amount of carbon dioxide ($CO_2$) generated when the coal is combusted may also be reduced.

A method of producing an SNG will be explained in detail with reference to FIG. 1.

First, a first gasification unit 110 and a second gasification unit 120 are used as a gasification device for generating carbon monoxide (CO) and hydrogen ($H_2$). Carbon monoxide (CO) and hydrogen ($H_2$) are generated in the first gasification unit 110 by reacting coal with water ($H_2O$) and oxygen ($O_2$), and hydrogen ($H_2$) is generated in the second gasification unit 120 by reacting aluminum powder with water ($H_2O$) and a catalyst. Since an oxide film is easily formed on a surface when a metal fuel such as the aluminum powder contacts air, if the aluminum powder is directly injected into the first gasification unit 110, which is optimized for a reaction of the coal, the process of the first gasification unit may not be continuously performed due to the oxide film. Accordingly, the aluminum powder is reacted in the second gasification unit 120, which is optimized for the process for reacting the aluminum powder with water ($H_2O$) and the catalyst, and steam in which hydrogen ($H_2$) is absorbed and heat is fed to the first gasification unit 110. Since hydrogen ($H_2$) and heat are fed to the first gasification unit 110 from the second gasification unit 120, gasification may be performed by using a relatively small amount of coal and energy.

Next, the carbon monoxide and the hydrogen discharged from the first gasification unit 110 are fed to a gas cleaning unit 200 in which impurities such as sulfur (S) or carbon dioxide ($CO_2$) are removed. In this case, since the metal fuel is used in the present exemplary embodiment, the amount of coal used is reduced, and thus the amount of impurities, such as carbon dioxide ($CO_2$), generated when the coal is combusted may also be reduced. Accordingly, a time taken to perform gas cleaning may be reduced and the emission of carbon dioxide, which is a greenhouse gas, may be reduced.

Next, the carbon monoxide and the hydrogen from which the impurities are removed are fed to a methanation unit 300 to generate methane through methanation according to the following process.

$$CO + 3H_2 \rightarrow CH_4 + H_2O \quad \text{(Equation 2)}$$

The methane may be used as an SNG for power generation, industrial use, and domestic use.

Accordingly, when an SNG is produced by using the method illustrated in FIG. 1, since methane is generated by replacing part of coal with a metal fuel, the amount of coal, which generates a lot of carbon dioxide ($CO_2$), used may be reduced, thereby reducing environmental pollution.

Meanwhile, aluminum oxide ($Al_2O_3$) is generated in the second gasification unit 120 after the process of reacting the aluminum powder with water ($H_2O$) and the catalyst. The aluminum oxide ($Al_2O_3$) may be reduced and reused by using the following process.

$$2Al_2O_3 + 3C \rightarrow 4Al + 3CO_2 \quad \text{(Equation 3)}$$

Figure 2:
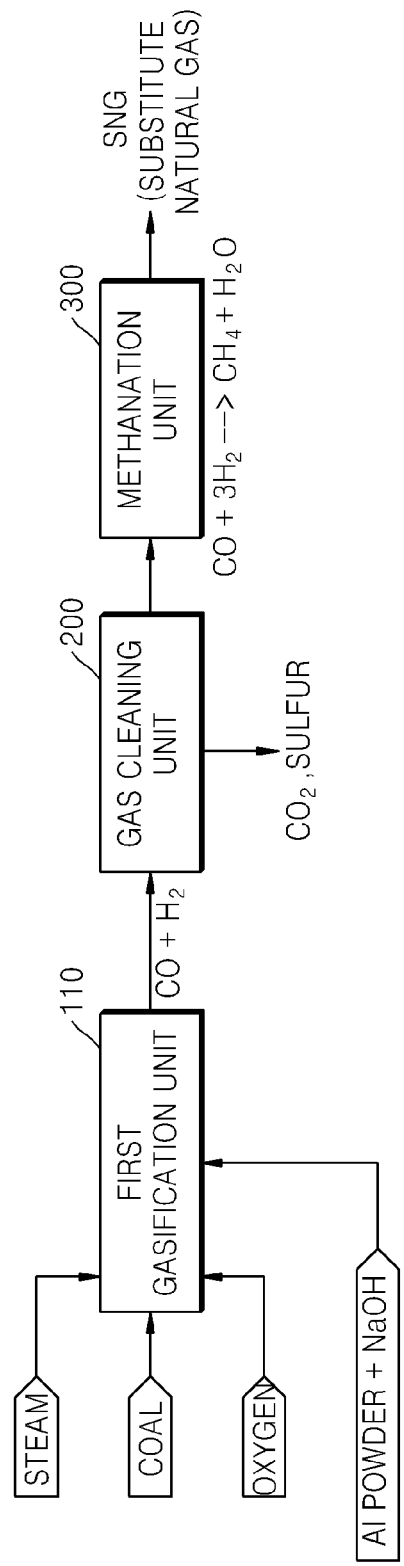
FIG. 2 is a block diagram illustrating a method of producing an SNG, according to another exemplary embodiment.

FIG. 2 is a block diagram for explaining a method of producing an SNG, according to another exemplary embodiment.

Referring to FIG. 2, both coal and a metal fuel are used as sources of carbon monoxide and hydrogen.

However, aluminum powder as the metal fuel is not reacted in the second gasification unit 120 as shown in the previous exemplary embodiment shown in FIG. 1, but is reacted in the first gasification unit 110 in which the coal is combusted. In this case, an oxide film generated on a surface of the aluminum powder may become a problem as described above. However, sodium hydroxide (NaOH), which is an alkaline material, is injected along with the aluminum powder in order to remove the oxide film. Instead of the sodium hydroxide, potassium hydroxide (KOH) or gallium may be injected. The following explanation will be given assuming that sodium hydroxide is used in the present exemplary embodiment. The aluminum powder is reacted in the first gasification unit 110 according to the following process to generate hydrogen.

$$2Al + 6H_2O + 2NaOH \rightarrow 2NaAl(OH)_4 + 3H_2 \quad \text{(Equation 4)}$$

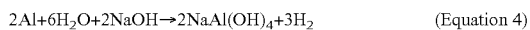

Since an alkaline material is also injected and thus the aluminum and oxygen are reacted with each other to prevent an oxide film from being generated, hydrogen may be continuously generated.

If potassium hydroxide is injected, a reaction occurs according to the following process and an oxide film may be prevented from being generated on a surface.

$$2Al + 6H_2O + 2KOH \rightarrow 2KAl(OH)_4 + 3H_2 \quad \text{(Equation 5)}$$

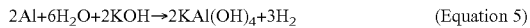

With respect to gallium, gallium is not reacted and instead suppresses a reaction between aluminum and oxygen.

Accordingly, since an oxide film is prevented from being generated by injecting such an alkaline material along with the aluminum powder into the first gasification unit 110, hydrogen may be continuously generated from the aluminum powder. That is, the coal and the aluminum powder are reacted in the first gasification unit 110, and the coal generates hydrogen and carbon monoxide and the aluminum powder generates hydrogen by reacting with water.

Next, the carbon monoxide and the hydrogen discharged from the first gasification unit 110 are fed to the gas cleaning unit 200 to remove impurities such as sulfur or carbon dioxide. In this case, since such a metal fuel is used, the amount of coal used is reduced, and thus the amount of impurities, such as carbon dioxide, generated when the coal is combusted may be reduced. Accordingly, a time taken to perform gas cleaning may be reduced and a burden of discharging carbon dioxide, which is a greenhouse gas, may be reduced.

Next, the carbon monoxide and the hydrogen from which the impurities are removed are fed to the methanation unit 300 to generate methane through methanation according to the process 2.

The methane may be used as an SNG for power generation, industrial use, and domestic use.

Accordingly, when an SNG is produced by using the method illustrated in FIG. 2, since methane is generated through methanation by replacing part of coal with a metal fuel, the amount of coal, which generates a lot of carbon dioxide, used may be reduced, thereby reducing environmental pollution.

As described above, a method of producing an SNG according to the present invention has the following effects.

First, since a metal fuel is supplied along with coal, hydrogen is generated from the metal fuel, and the hydrogen is supplied, the amount of coal needed to generate methane through methanation may be reduced and the amount of carbon dioxide generated when the carbon is combusted may also be reduced.

Second, since a process of generating hydrogen from a metal fuel is an exothermic reaction, energy needed to perform gasification may be less than that when only coal is used.

Third, when a reaction for removing an oxide film generated on a surface of a metal fuel is also performed, methanation may be smoothly performed even by using a single gasification unit.

The exemplary embodiments are for the production of an SNG used for power generation, industrial use, and domestic use.

While the exemplary embodiments have been particularly shown and described above, it will be understood by those of ordinary skill in the art that various changes in form and details may be made therein without departing from the spirit and scope of the present inventive concept as defined by the following claims.

What is claimed is:

1. A method of producing a substitute natural gas (SNG), the method comprising:
   generating carbon monoxide and hydrogen using coal and a metal fuel, the generating the carbon monoxide and the hydrogen comprising:
      generating the carbon monoxide and primary hydrogen by gasifying the coal in a first gasification unit; and
      generating secondary hydrogen by reacting the metal fuel in a second gasification unit;
   generating methane from the generated carbon monoxide and primary hydrogen;
   generating secondary hydrogen by reacting the metal fuel in the second gasification unit; and
   supplying heat generated from the generating of the secondary hydrogen in the second gasification unit to the first gasification unit.

2. The method of claim 1, wherein the generating of the carbon monoxide and the hydrogen further comprises supplying the secondary hydrogen generated in the second gasification unit to the first gasification unit.

3. The method of claim 2, further comprising:
   generating a metal oxide by reacting the metal fuel in the second gasification unit; and
   reducing and reusing the metal oxide as the metal fuel.

4. The method of claim 2, wherein the metal fuel comprises aluminum powder or magnesium powder.

5. The method of claim 3 further comprising removing impurities from the generated carbon monoxide and hydrogen in a gas cleaning unit.

6. The method of claim 1, wherein the generating of the carbon monoxide and the hydrogen comprises generating carbon monoxide and hydrogen by gasifying both the coal and the metal fuel in the first gasification unit.

7. The method of claim 6 further comprising adding an alkaline material along with the metal fuel to the first gasification unit.

8. The method of claim 7, wherein the metal fuel comprises aluminum powder or magnesium powder, and the alkaline material is selected from the group consisting of sodium hydroxide, potassium hydroxide, and gallium.

9. The method of claim 6, wherein the gasifying both the carbon monoxide and the hydrogen comprises:
   generating the carbon monoxide and primary hydrogen by reacting the coal with water and oxygen; and
   generating secondary hydrogen by reacting the metal fuel with water and a catalyst.

10. The method of claim 9, further comprising generating heat from the generating the secondary hydrogen by reacting the metal fuel with the water and the catalyst.

11. The method of claim 6 further comprising removing impurities from the generated carbon monoxide and hydrogen in a gas cleaning unit.

12. The method of claim 1, wherein the supplying the heat generated from the generating of the secondary hydrogen comprises supplying steam generated from the generating of the secondary hydrogen to the first gasification unit for the generating the carbon monoxide and the primary hydrogen.

13. The method of claim 12, wherein the supplying the steam comprises supplying the steam generated from the generating of the secondary hydrogen to the first gasification unit for the generating the carbon monoxide and the primary hydrogen to reduce an amount of coal used for the generating the carbon monoxide and the primary hydrogen.

* * * * *